(12) United States Patent
Costa et al.

(10) Patent No.: US 12,173,262 B2
(45) Date of Patent: Dec. 24, 2024

(54) DEVICES COMPRISING ORGANOID CHAMBERS AND USES THEREOF TO CULTURE, MAINTAIN, MONITOR OR TEST ORGANOIDS

(71) Applicant: Novoheart International Limited, Kowloon (HK)

(72) Inventors: Kevin D. Costa, Hong Kong (HK); Yosuke Kurokawa, Hong Kong (HK); Eugene K. Lee, Hong Kong (HK); David D. Tran, Hong Kong (HK); Bernard Fermini, Hong Kong (HK)

(73) Assignee: Novoheart International Limited, Kowloon (HK)

( * ) Notice: Subject to any disclaimer, the term of this patent is extended or adjusted under 35 U.S.C. 154(b) by 453 days.

(21) Appl. No.: 17/364,288

(22) Filed: Jun. 30, 2021

(65) Prior Publication Data

US 2021/0403844 A1 Dec. 30, 2021

Related U.S. Application Data

(60) Provisional application No. 63/046,435, filed on Jun. 30, 2020.

(51) Int. Cl.
*C12M 3/00* (2006.01)
*C12M 1/00* (2006.01)
*C12N 5/071* (2010.01)

(52) U.S. Cl.
CPC ............ *C12M 21/08* (2013.01); *C12M 23/22* (2013.01); *C12M 23/34* (2013.01); *C12N 5/0602* (2013.01); *C12N 2513/00* (2013.01)

(58) Field of Classification Search
None
See application file for complete search history.

(56) References Cited

U.S. PATENT DOCUMENTS

| 5,240,854 | A | * | 8/1993 | Berry | ..................... | C12M 23/04 |
| | | | | | | 435/305.1 |
| 2015/0072413 | A1 | * | 3/2015 | Zenhausern | ........... | C12M 29/04 |
| | | | | | | 156/291 |

(Continued)

FOREIGN PATENT DOCUMENTS

| CN | 2738750 Y | 11/2005 |
| CN | 106455541 A | 2/2017 |

(Continued)

OTHER PUBLICATIONS

Shah, R.R. Can pharmacogenetics help rescue drugs withdrawn from the market? Pharmacogenomics, 7(6):889-908 (2006).

(Continued)

*Primary Examiner* — Holly Kipouros
(74) *Attorney, Agent, or Firm* — K&L Gates LLP; Louis C. Cullman; Giorgios N. Kefallinos

(57) ABSTRACT

Provided are multi-layer bioreactors for growing, maintaining, stimulating, monitoring and testing organoids and tissues derived from or representing hollow organs in organoid chambers. Also provided are uses of those bioreactors in modeling a disease process for monitoring disease progress and/or for assessing a biological effect, such as therapeutic efficacy and/or toxicity, e.g., organotoxicity. Also disclosed are bioreactors comprising organoid chambers that are useful as systems for measuring the volume, pressure, contractility, pump function, or electrophysiology of an organoid chamber as well as systems for controlling the pressure experienced by an organoid or tissue in an organoid chamber.

21 Claims, 7 Drawing Sheets

(56) References Cited

U.S. PATENT DOCUMENTS

| | | | |
|---|---|---|---|
| 2016/0333295 A1* | 11/2016 | Baker | .................... C12M 23/16 |
| 2017/0107469 A1* | 4/2017 | Costa | .................... C12M 23/26 |
| 2017/0355940 A1 | 12/2017 | Neumann et al. | |
| 2021/0002596 A1* | 1/2021 | Catarino Ribeiro | ... C12M 25/14 |
| 2021/0371790 A1* | 12/2021 | Macqueen | ......... G01N 33/5088 |
| 2023/0257711 A1 | 8/2023 | Roberts et al. | |

FOREIGN PATENT DOCUMENTS

| | | |
|---|---|---|
| CN | 106536707 A | 3/2017 |
| WO | 2018/071354 A1 | 4/2018 |
| WO | 2018/140497 A1 | 8/2018 |
| WO | 2019/172756 A1 | 9/2019 |
| WO | 2019/156941 A9 | 12/2019 |
| WO | 2022/150626 A1 | 7/2022 |

OTHER PUBLICATIONS

Dimasi et al., Innovation in the pharmaceutical industry: New estimates of R&D costs. J. Health Econ. 47:20-33 (2016).

Mercola et al., Induced pluripotent stem cells in cardiovascular drug discovery. Circ Res. 112:534-548 (2013).

Passier et al., Complex Tissue and Disease Modeling using hiPSCs. Cell Stem Cell, 18:309-321 (2016).

Li et al., Bioengineering an electro-mechanically functional miniature ventricular heart chamber from human pluripotent stem cells. Biomaterials, 163: 116-127 (2018).

Extended European Search Report, mailed Nov. 18, 2021, for European Patent Application No. 21182742.3 filed on Jun. 30, 2021, search completed on Nov. 10, 2021.

Roberts el al., "Ultra-Compliant Indwelling Elastomer Balloons Improve Stability and Performance of Bioengineered Human Mini-Hearts," Advanced Engineering Materials, vol. 24, 8, Feb. 2, 2022 (Feb. 2, 2022).

* cited by examiner

DEVICES COMPRISING ORGANOID CHAMBERS AND USES THEREOF TO CULTURE, MAINTAIN, MONITOR OR TEST ORGANOIDS

CROSS-REFERENCE TO RELATED APPLICATIONS

The present application claims the benefit of U.S. Provisional Application 63/046,435 filed Jun. 30, 2021, the entire contents of which is incorporated by reference herein.

FIELD

The disclosed subject matter relates to the field of devices for use in culturing, maintaining, monitoring, or testing organoids and tissues.

BACKGROUND

The ability to accurately detect toxicity and efficacy, particularly towards the heart, remains a considerable challenge in the development of new drugs. Models of human heart disease are needed to develop effective therapies, and existing models are imperfect, as shown by the frequency with which compounds showing promise in a model system fail to exhibit efficacy in clinical trials. In addition, cardiotoxicity has caused significant attrition of candidate compounds as well as post-market drugs, contributing to the exorbitant cost of drug development [1,2]. Due to intrinsic fundamental differences in the physiology of the human heart compared to traditional experimental animal models, researchers have focused efforts on developing in vitro models using cardiomyocytes derived from human pluripotent stem cells that can better predict the human-specific response to a compound of interest [3].

While many such in vitro human stem cell models have been developed over the years, most have focused on simple designs that minimally recapitulate the functions of the heart. The models have limited outputs that can be insufficient in studying a response to a compound of interest. For example, a monolayer of cardiomyocytes can be useful in studying cardiac electrophysiology but is limited in the ability to study inotropic agents that require a measure of contractile force. Simple 3D models such as cardiac tissue strips can be used to study changes in developed force but lack outputs that are more clinically relevant such as pressure-volume relationship, ejection fraction, and stroke work. The lack of physiological relevance also restricts the capability of the models to recapitulate many disease phenotypes needed for efficacy testing, especially since heart diseases are often inextricably linked to the hemodynamic loading conditions on the heart. Thus, there is a need for more biologically complex cardiomimetic human in vitro models that can provide additional insights in both drug development and disease modeling [4].

One such model is the cardiac organoid chamber (COC), which consists of a cardiac tissue in a 3D shape with a hollow center [5]. By accessing the inner volume of the COC, the model can produce clinically relevant outputs for studying cardiac physiology and pathophysiology. However, fabrication and culture of the COC is a complex and delicate process, and performing experiments using the COC presents significant technical challenges. In addition, the current COC design has a single inlet/outlet and thus cannot have independent control of inlet conditions (preload) and outlet conditions (afterload), which can be critical in studying various forms of heart failure. Described herein is the design of a bioreactor system that improves fabrication, culture, and testing of organoid chambers (OCs), including cardiac organoid chambers (COCs).

SUMMARY

The disclosure provides versatile devices for culturing cells in an environment that promotes formation of organoids and tissues, and particularly those organoids and tissues derived from hollow organs, that more closely mimic the naturally occurring organs and tissues as they are found in vivo. The devices are therefore useful in producing and maintaining organoids and tissue(s) as well as providing a contained environment for monitoring the development and/or behavior of the living material and for testing that material, such as by observing the effect of added compounds or the effect of biophysical stimulation, e.g., electrical, mechanical, pH, osmolarity, temperature, hormonal, and the like. For example, electrical stimulation can involve pacing pulses delivered to the organoids and/or tissues. The modular design increases the versatility of the devices while keeping manufacturing costs to a minimum.

The bioreactor for fabricating and testing organoid chambers (OCs) includes a top section that directs the flow of fluid in and out of the OC, a middle section that holds the OC, and a bottom section for holding the culture medium that surrounds and nourishes the OC. Additional components can include any of the following: a system for electrically stimulating the OC, a system for measuring changes in the pressure, volume, and/or electrophysiology of the OC, and a system for controlling the preload and afterload applied on the OC. Exemplary OCs are cardiac organoid chambers (COCs).

The top layer of the bioreactor contains an inlet and an outlet that feed to the internal volume of the OC through the middle layer. One or more valves separate the inlet and the outlet, which allow for independent control of the applied pressure at the inlet (i.e., preload) and the outlet (i.e., afterload). Any valve type known in the art that is compatible with the bioreactor configuration is contemplated as suitable for inclusion in the bioreactor. Such a system enables independent control of preload and afterload of the OC, which can be used to study pathological conditions such as heart failure with preserved ejection fraction (HFpEF).

In some exemplary embodiments, the integrated valves have been developed to match the actuation pressure with the developed pressure of the OC. Each valve consists of a thin sheet of elastomeric material that is cut to allow local displacement of the sheet, which is sandwiched between 2 layers of rigid plastic sheets that serve as a backing for the valve layer. The rigid backing has cut openings that differ on one side of the valve versus the other to enable flow of fluid to preferentially occur in one direction. The properties and/or geometry of the valves can be modified to study pathological conditions such as valvular stenosis.

The bioreactor is designed to allow fabrication and culture of the OC without the top layer attached. The modular design allows for increased throughput by culturing multiple OCs without the top layer. By using a simple attachment mechanism (e.g., Luer fittings such as Luer-slip fittings), the top layer is easily attached when necessary for testing the OC. Such a mechanism enables longitudinal studies, as the top layer can be detached and the OC can be returned to the incubator for extended culture periods.

In one aspect, the disclosure provides a bioreactor for an organoid or tissue derived from a hollow organ comprising:

(a) a top layer for directing fluid flow into and/or out of an organoid chamber comprising an organoid or tissue; (b) a middle layer, wherein the middle layer comprises the point of attachment for the organoid chamber; and (c) a bottom layer comprising a reservoir for culture fluid; wherein the top layer and middle layer are in fluid communication capable of exchanging an internal fluid (relative to the organoid chamber), wherein the top layer, middle layer and bottom layer are in fluid communication capable of exchanging an external fluid (relative to the organoid chamber); and wherein the organoid or tissue comprises a barrier between the internal fluid and the external fluid. In some embodiments, the point of attachment for the organoid chamber comprises a blunt needle attached at one end to the middle layer and attached at the other end to the organoid chamber. In some embodiments, the organoid chamber further comprises an elastomeric lining material providing an impermeable barrier between the internal fluid and the external fluid. In some embodiments, the elastomeric material is a balloon. In some embodiments, the organoid or tissue is derived from cells of a heart, a lung, a gall bladder, a urinary bladder, a blood vessel, a lymph vessel, a ureter, a urethra, a small intestine, or a colon or other hollow organ or tissue. In some embodiments, the cells are derived from pluripotent stem cells. In some embodiments, the top layer comprises a bottom surface comprising a Luer fitting (e.g., a male or female Luer-slip end) terminating a fluid channel in the top layer, wherein the Luer fitting (e.g., male or female Luer-slip end) connects to the top surface of the middle layer (e.g., a complementary Luer-slip end), thereby providing a channel for fluid communication between the top layer and the middle layer. In some embodiments, the fluid channel in the top layer terminates in an inlet port and in an outlet port in the top surface of the top layer. In some embodiments, the bioreactor further comprises a first flangeless fitting for connecting the inlet port to an external fluidic line and a second flangeless fitting for connecting the outlet port to a second external fluidic line. In some embodiments, the bioreactor further comprises at least one valve to control the flow of fluid in the channel of the top layer. In some embodiments, the at least one valve allows one-way fluid flow from the inlet port to the outlet port. In some embodiments, the bioreactor further comprises two layers of a plastic (e.g., polycarbonate) or metal sheet containing a valve layer therebetween, wherein the valve layer comprises the at least one valve to control the flow of fluid. In some embodiments, a gasket is interposed between the valve layer and each layer of plastic or metal sheet. In some embodiments, the two layers of plastic or metal sheet and the valve layer are attached using fasteners, a solvent, a sealant, or glue. In some embodiments, the fasteners are screws, threaded inserts, nut traps, clamps, latches, snap fittings, or press fittings, used alone or in any combination.

In some embodiments, the top layer further comprises a measurement channel for a measurement device, wherein the measurement channel is in fluid communication with the internal fluid channel of the top layer, and wherein the measurement channel terminates at a side surface of the top layer in a measurement port. In some embodiments, the measurement channel comprises a measurement device. In some embodiments, the measurement device is a pressure transducer. In some embodiments, the living cells form an organoid or at least one tissue around the elastic balloon. In some embodiments, the bioreactor further comprises a blunt needle that terminates in an internal volume of the organoid chamber and traverses the middle layer of the bioreactor. In some embodiments, the bottom surface of the middle layer comprises a groove. In some embodiments, the bottom surface of the middle layer and the top surface of the bottom layer provide mating surfaces that register the surfaces relative to each other. In some embodiments, the bottom surface of the middle layer comprises a groove and the top surface of the bottom layer comprises a complementary mating surface to the bottom surface of the middle layer comprising the groove, or wherein the top surface of the bottom layer comprises a groove and the bottom surface of the middle layer comprises a complementary mating surface to the top surface of the bottom layer comprising the groove. In some embodiments, the middle layer is fabricated from a single sheet of plastic (e.g., polycarbonate) or metal. In some embodiments, the middle layer further comprises a perfusion inlet port and a perfusion outlet port. In some embodiments, the middle layer further comprises an electrical system comprising at least one electrode, wherein each electrode is positioned to provide an electrical stimulation to the organoid chamber, to electrically record a signal from the organoid chamber, or both. In some embodiments, at least one electrode is in contact with the organoid chamber. In some embodiments, each electrode is made of carbon, platinum, gold, or any conductive material known in the art to be compatible with electrical stimulation of living cells. In some embodiments, two electrodes are disposed 180 degrees from each other. In some embodiments, each electrode is positioned by at least one O-ring. In some embodiments, the at least one electrode is a bipolar electrode (a) in contact with the exterior surface of the organoid chamber comprising the organoid or at least one tissue, or (b) integrated into a point where the blunt needle is attached to the middle layer. In some embodiments, the middle layer further comprises a system for sensing electrophysiological changes in the organoid or tissue of the organoid chamber.

In some embodiments, the bottom layer comprises culture fluid in contact with the exterior of the organoid chamber. In some embodiments, the bottom layer is composed of a material that is biocompatible and optically transparent. In some embodiments, the material is acrylic, polystyrene, glass or polycarbonate. In some embodiments, the bottom layer further comprises at least one flat window for observation of the organoid chamber. It will be appreciated that bioreactors comprising an observation window in the bottom layer can be otherwise transparent, translucent or opaque. In some embodiments, the bottom layer comprises at least one port, at least one valve, or at least one port and at least one valve, wherein the at least one port and/or at least one valve provides for exchanging fluid or adding at least one compound. In some embodiments, the bottom layer comprises an electrode for stimulating the organoid or tissue. In some embodiments, fluid channels of different layers are connected using Luer fittings, threaded connectors, magnetic connectors or a snap-fit geometric design. In some embodiments, a male Luer-slip end at the bottom surface of the top layer is connected to a female Luer-lock end at the top surface of the middle layer, and embodiments are envisioned in which the male and female Luer-lock ends are switched. In some embodiments, the middle layer and the bottom layer are sufficient to culture the organoid or tissue in an incubator. In some embodiments, the bioreactor further comprises a system for measuring an electrophysiological property of the organoid or tissue. In some embodiments, the system comprises at least one sensing electrode for measuring the extracellular potential of the organoid or tissue in the organoid chamber. In some embodiments, the sensing electrode is in direct contact direct contact with the interior or exterior of the organoid chamber. In some embodiments, there are a plurality of sensing electrodes that do not directly contact the organoid chamber, wherein the plurality of sensing electrodes detect the electrical signal from the organoid chamber.

Another aspect of the disclosure is drawn to a use of the bioreactor disclosed herein to culture, maintain, stimulate, monitor or assay the organoid or tissue in the organoid chamber. In exemplary embodiments, the bioreactor is useful in modeling disease processes by developing organoids and tissues using cells and tissues associated with disease to model, e.g., human disease, for example heart disease. Bioreactors comprising a diseased organoid or tissue are useful in monitoring disease progress and in testing or assaying candidate therapeutics for efficacy. In some embodiments, the use extends to addition of the compound (a candidate therapeutic or a compound having been shown to be efficacious in treating a disease) to the culture medium and observation of the effect on the organoid or tissue, thereby assaying the compound for a biological effect, such as toxicity (e.g., organotoxicity). In some embodiments, the effect is an altered organoid or tissue stiffness, pressure, volume, or growth rate. In some embodiments, the effect is an alteration in electrophysiology. In some embodiments, the organoid or tissue is a cardiac organoid or tissue.

Yet another aspect of the disclosure is a system to measure the volume of or pressure experienced by an organoid chamber comprising the bioreactor disclosed herein and a measurement device. In some embodiments, the device to measure volume is a camera, a pressure-volume catheter placed into the interior volume of the organoid chamber, a flow meter for measuring internal fluid flow, or an ultrasonic transducer to image the organoid chamber. In some embodiments, the device to measure volume is a camera, the system further comprising at least one fiducial marker attached to the surface of the organoid chamber. In some embodiments, the at least one fiducial marker is tracked optically or magnetically.

Still another aspect of the disclosure is a system for controlling pressure within an organoid chamber comprising the bioreactor disclosed herein and a pressure controller attached to the inlet port of the top layer, to the outlet port of the top layer, or to both the inlet and outlet ports of the top layer, to regulate the fluid pressure applied to the organoid chamber. In some embodiments, the organoid is a cardiac organoid and the pressure applied to the organoid chamber is automatically controlled. In some embodiments, the pressure is dynamically controlled to mimic cardiac physiology. In some embodiments, the pressure is controlled using hydrostatic pressure or using at least one fluid pump.

Other features and advantages of the disclosure will be better understood by reference to the following detailed description.

DETAILED DESCRIPTION

The disclosure provides a versatile, compact platform for developing, monitoring and testing organoids and tissues derived from hollow organs that mimics the natural environment of these organs by maintaining a hollow interior of the organoids or tissues. The platform provides devices that allow for culture medium changes, additions to culture medium being delivered to the organoid/tissue, monitoring of appearance, size, contractility, pump function, and electrophysiology of the organoids/tissues, electrical stimulation of the organoids/tissues, and detection of mechanical and electrophysiological changes in the organoids/tissues, all in a device that can be economically and quickly produced for single or multiple uses. In the following description of the various aspects of the disclosure, reference is made to the figures.

Figure 1:
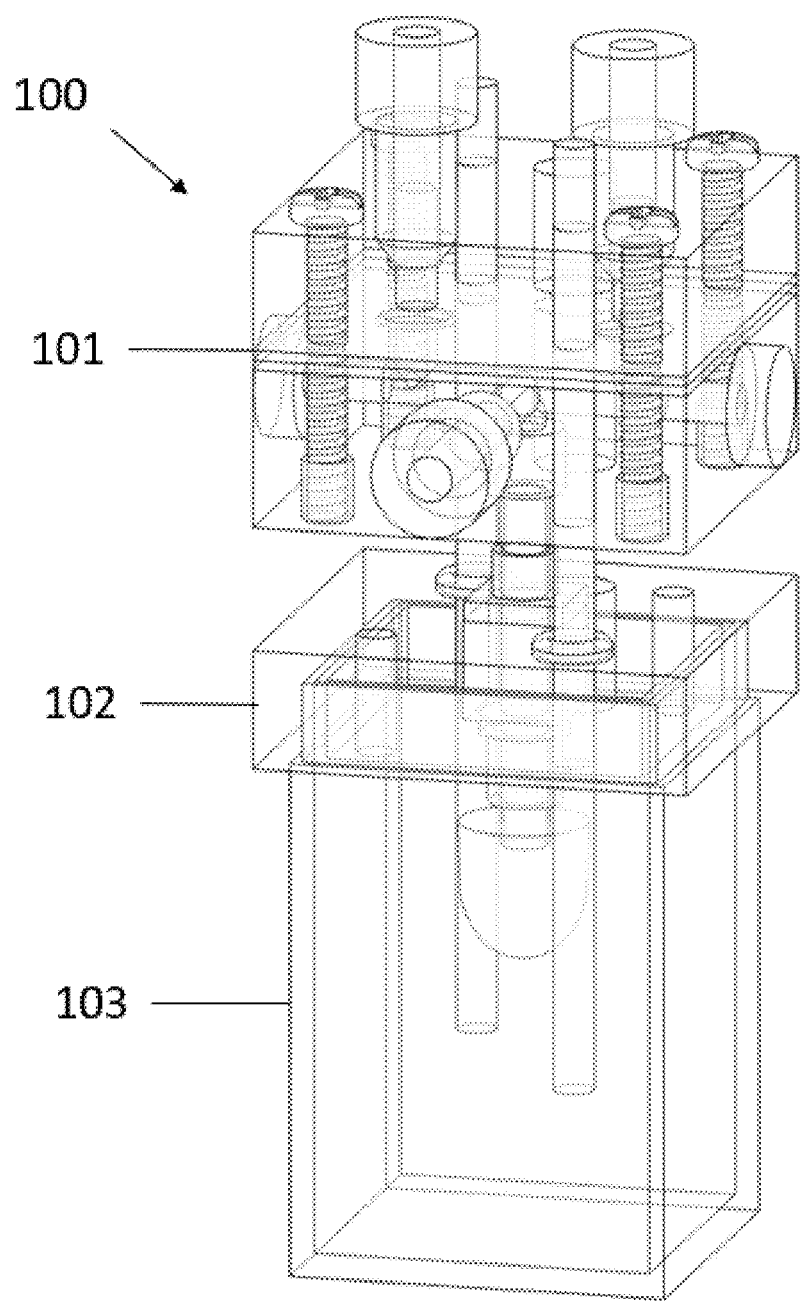
FIG. 1 illustrates the organoid chamber (OC) bioreactor in its assembled form.

FIG. 1 shows that organoid chamber (OC) bioreactor 100 consists of 3 main layers: top layer 101 that directs the flow of fluid in and out of OC 300 (See FIG. 3), middle layer 102 that holds OC 300, and bottom layer 103 that holds the medium for culturing an organoid or one or more tissues within OC 300. The bioreactor is designed for fabrication, culture, and testing of a cardiac organoid or any other hollow organ or tissue (e.g., heart, lung, gall bladder, urinary bladder, blood vessel, lymph vessel, small intestine, colon, and the like) that involve separate access to the internal and external volumes of the organoid or tissue.

Top layer 101 as a unit controls the flow of internal fluid. Bottom layer 103 serves as a reservoir for fluid 400 (see FIG. 4), which is culture medium in some embodiments, used to culture the organoid or tissue of OC 300. The main function of middle layer 102 is to serve as the ultimate attachment point of OC 300 to bioreactor 100. Organoids are grown around the end of blunt needle 301 (see FIG. 3A) at the bottom of middle layer 102 and remain attached there during the entire culture and testing periods. Blunt needle 301 is part of middle layer 102, and therefore OC 300 is considered to be part of middle layer 102.

Figure 3A:
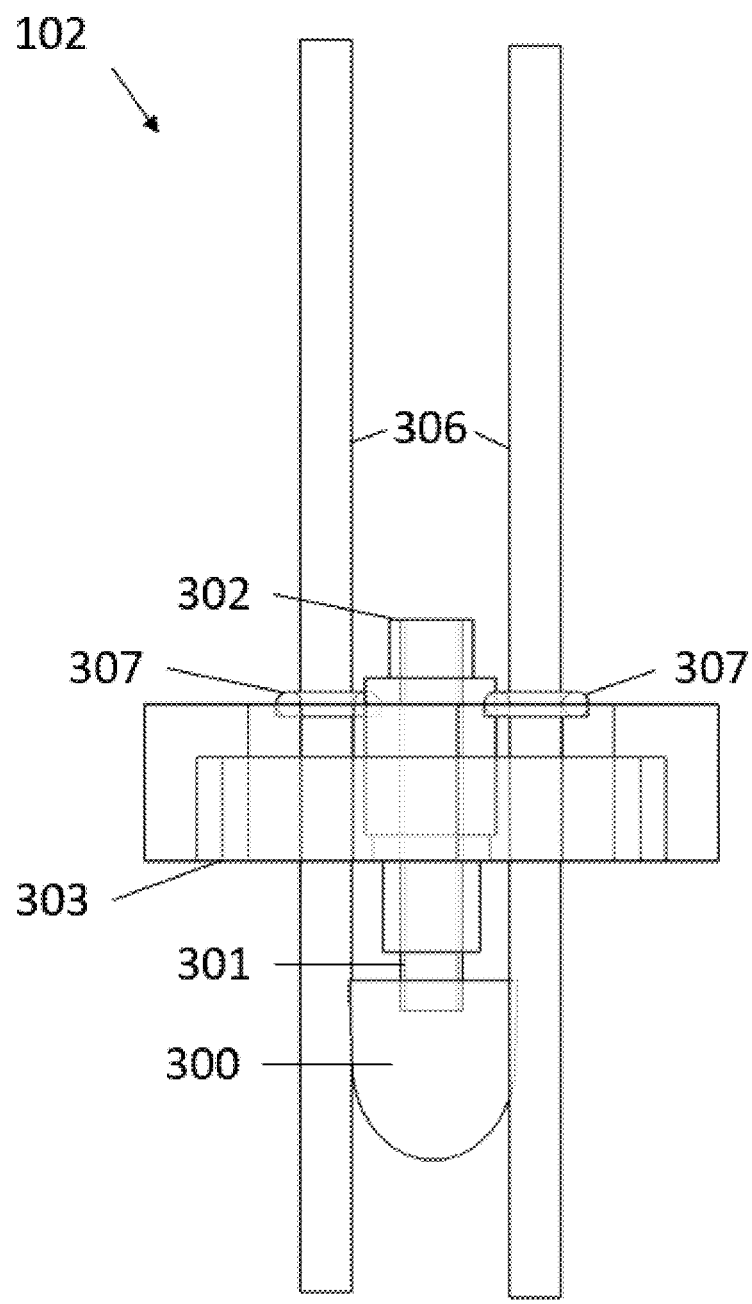
FIG. 3A illustrates the middle layer of the OC bioreactor.

Positionally, OC 300 does occupy the internal cavity of bottom layer 103. However, when the three layers are separated, OC 300 remains anchored to middle layer 102 as shown in FIG. 3A. Similarly, electrodes 306 (FIG. 3A) extend into both the top layer 101 and bottom layer 103, but remain attached to middle layer 102 when the layers are separated.

Figure 2A:
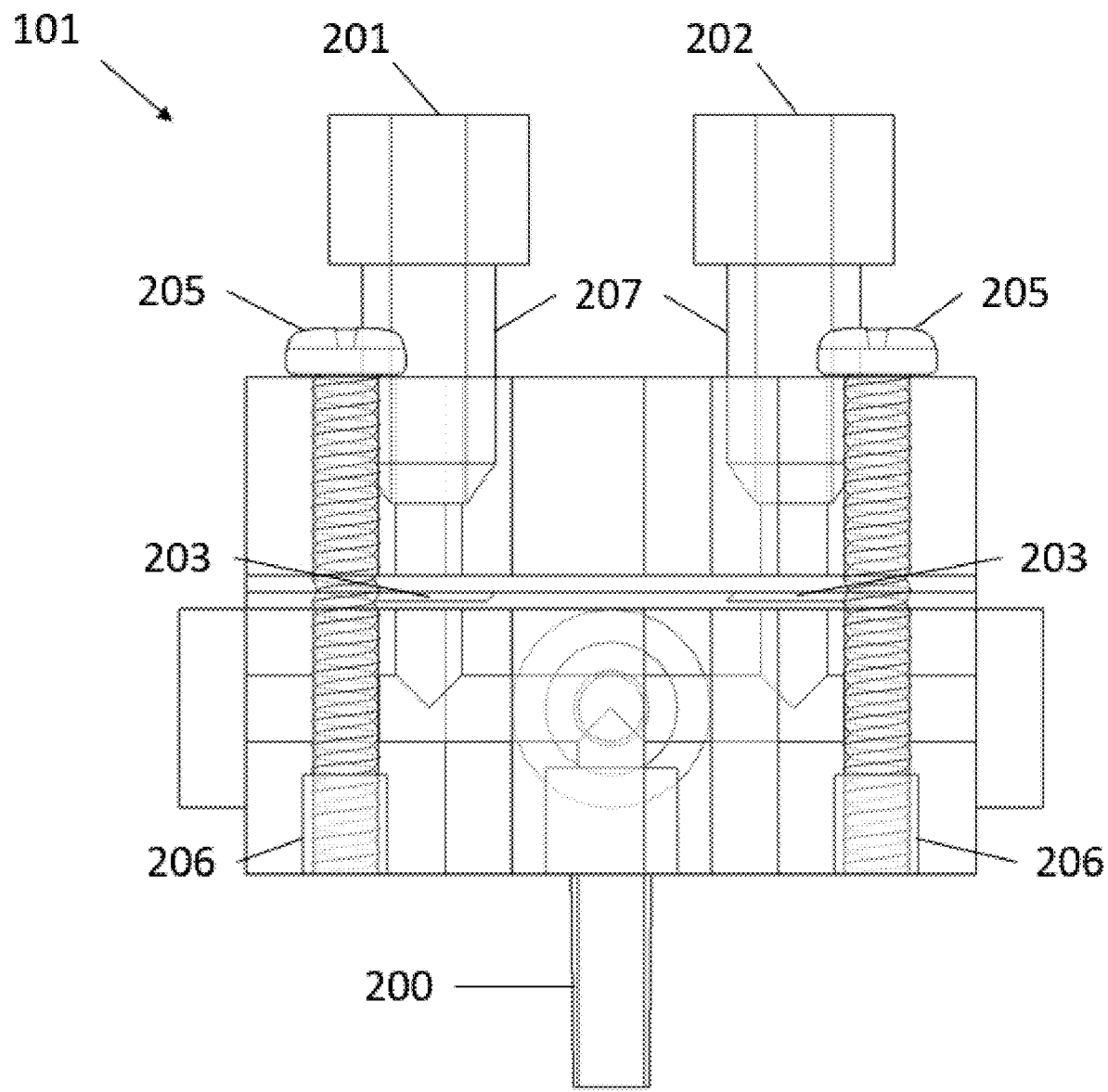
FIG. 2A illustrates the top layer of the OC bioreactor.
Figure 2B:
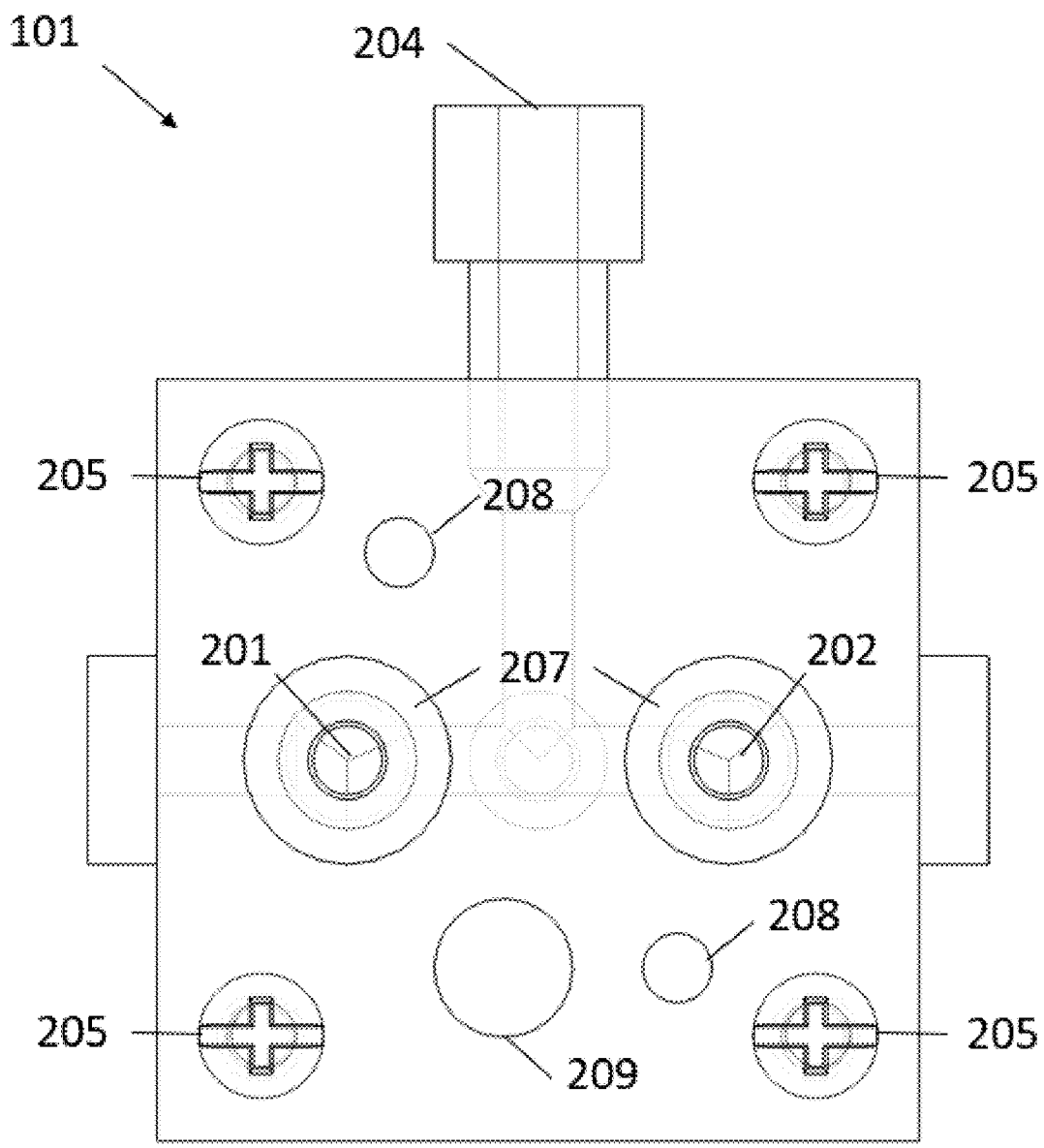
FIG. 2B illustrates a top view of the top layer of the OC bioreactor.

In reference to FIG. 2A, top layer 101 of OC bioreactor 100 has fluidic components as required to flow solution in and out of the internal volume of OC 300 (see FIG. 3A). In some embodiments, OC 300 contains an organoid and/or tissue(s) and in some embodiments, OC 300 further comprises a non-biological lining material (e.g., a support material) such as an elastomeric material, e.g., an elastomeric balloon. Male Luer-slip end 200 is positioned at the bottom surface of top layer 101 terminating a fluid channel in top layer 101. Male Luer-slip end 200 connects to the top surface of middle layer 102 to provide a channel for fluid communication between top layer 101 and middle layer 102. When male Luer-slip end 200 is connected to middle layer 102, a fluid communication channel between top layer 101 and middle layer 102 is established. The bottom opening of top layer 101 is part of a fluid communication channel that branches to two openings on the top surface of top layer 101, and those two openings serve as inlet 201 and outlet 202 for the internal fluid. A valve 203, or a plurality thereof, regulates the flow of fluid from inlet 201 to outlet 202. The valves 203 allow flow to preferentially occur in one direction (i.e., from inlet 201 towards outlet 202) and also enables independent pressure loading at the inlet and the outlet. Top layer 101 contains a measurement channel for placing or inserting a measurement device such as a pressure transducer for measuring the pressure inside OC bioreactor 100. The measurement channel terminates at a surface, such as a side surface, of top layer 101 in measurement port 204.

In this embodiment, top layer 101 comprises two layers of polycarbonate sheets with a valve layer. The valve layer is positioned between the two polycarbonate sheets. The valves themselves are internal to the valve layer (and thus the top layer), but the valve layer is stacked as part of the top layer. The valve layer is made from a thin sheet of an elastomeric material known in the art, such as polydimethylsiloxane (PDMS) or similar elastomer with apertures or other features that allow fluid to pass through in one direction but resist fluid flow in the opposite direction. The polycarbonate sheets are milled to the desired design using a CNC router, milling machine, or similar manufacturing method. The three layers are fastened together using fasteners, such as screws 205 and threaded inserts or nut traps 206. A gasket may be placed between each of the layers to create a sealed, liquid-tight system. In other embodiments, an adhesive or sealant is used. Inlet 201 and the outlet 202 connect to external fluidic lines using a flangeless fitting 207. Vertical throughholes 208 exist on top layer 101 for at least one pacing electrode 306 (preferably a pair) and a feeding/withdrawal port 209 for accessing the external volume of OC 300.

In reference to FIG. 3A, middle layer 102 of OC bioreactor 100 holds OC 300 in place during culture and testing. An organoid or tissue(s), such as a cardiac organoid forms around a balloon to yield OC 300. The balloon is attached to the end of blunt needle 301 positioned in bottom layer 103. Thus, blunt needle 301 projects through both the top surface of bottom layer 103 and the bottom surface of middle layer 102. The other end of blunt needle 301 is a Luer fitting, e.g., female Luer-lock end 302, that is used to connect to top layer 101 of OC bioreactor 100. In some embodiments, middle layer 102 is positioned directly on top of bottom layer 103. On the bottom surface of middle layer 102, a groove 303 is preferably milled to fit the top surface of bottom layer 103.

Figure 3B:
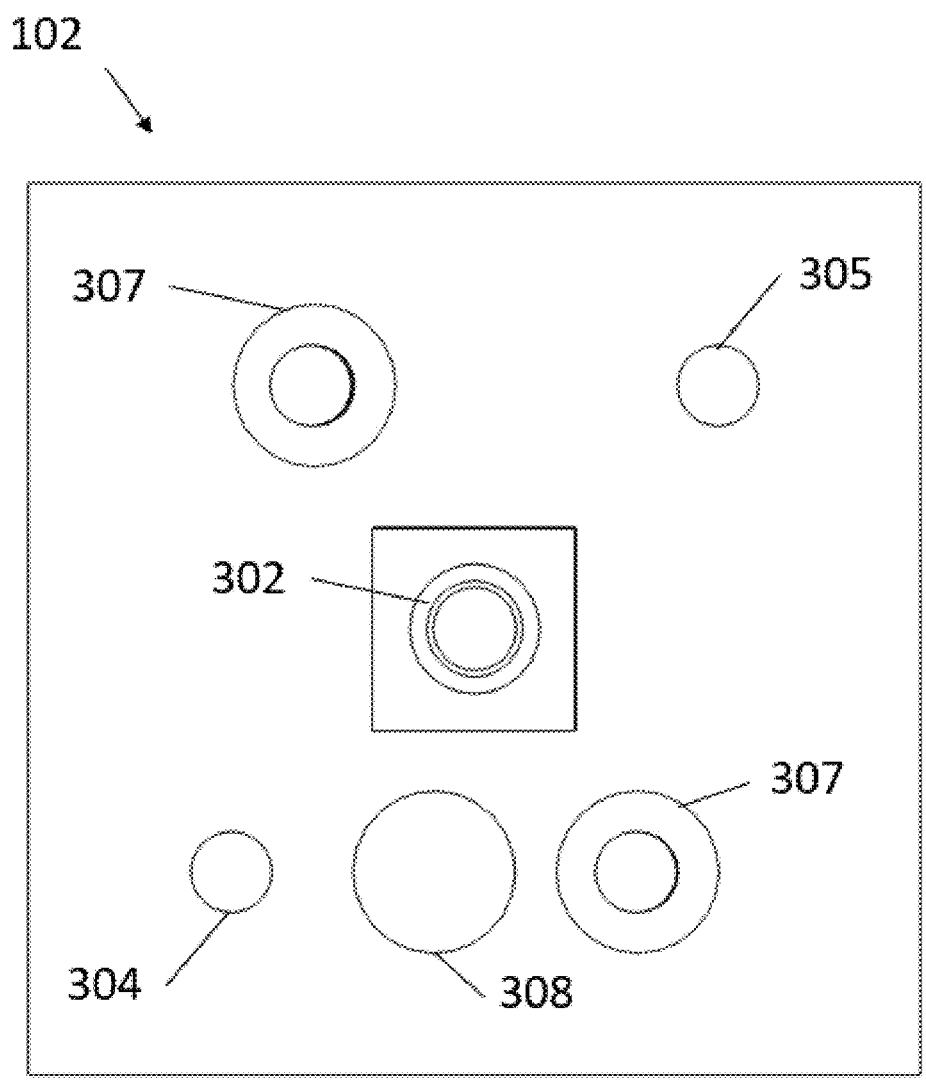
FIG. 3B illustrates a top view of the middle layer of the OC bioreactor.

In this embodiment, middle layer 102 is fabricated from a single sheet of polycarbonate using a CNC router. Middle layer 102 can have perfusion inlet port 304 and/or perfusion outlet port 305 for exchanging medium from bottom layer 103, i.e., the fluid in fluid communication with the exterior of OC 300. Additionally, middle layer 102 can have a feeding/withdrawal port 308 that aligns with analogous feeding/withdrawal ports 209 in top layer 101 to access fluid 400 (e.g., medium) in bottom layer 103 from top layer 101. Inlet port 201 and outlet port 202 of top layer 101 provide fluid communication channels in contact with the interior of OC 300. In this embodiment, as shown in FIG. 3B, a separate inlet perfusion port 304 and outlet perfusion port 305 are positioned towards opposite edges of middle layer 102. In some embodiments, the perfusion ports are attached to tubing suitable for use in cell culture. Middle layer 102 can have a system for electrically stimulating the organoid or tissue(s). In these embodiments, each electrode 306 (e.g., a carbon electrode) is positioned towards, and penetrates, opposite edges of middle layer 102 to provide a source of electrical stimulation on opposing sides of OC 300 contained within middle layer 102. Each electrode 306 is held in place using at least one O-ring 307. In another embodiment, a system for performing point stimulation of the organoid or tissue(s) is used. Such a system can position a bipolar electrode directly onto the surface of the organoid or tissue(s), or OC 300, or be integrated at the attachment point of OC 300 to middle layer 102. Middle layer 102 may also have a system for sensing changes in the electrophysiology of the organoid or tissue(s) of OC 300 using sensing electrodes 306 in a manner similar to that of an electrocardiogram.

Figure 4:
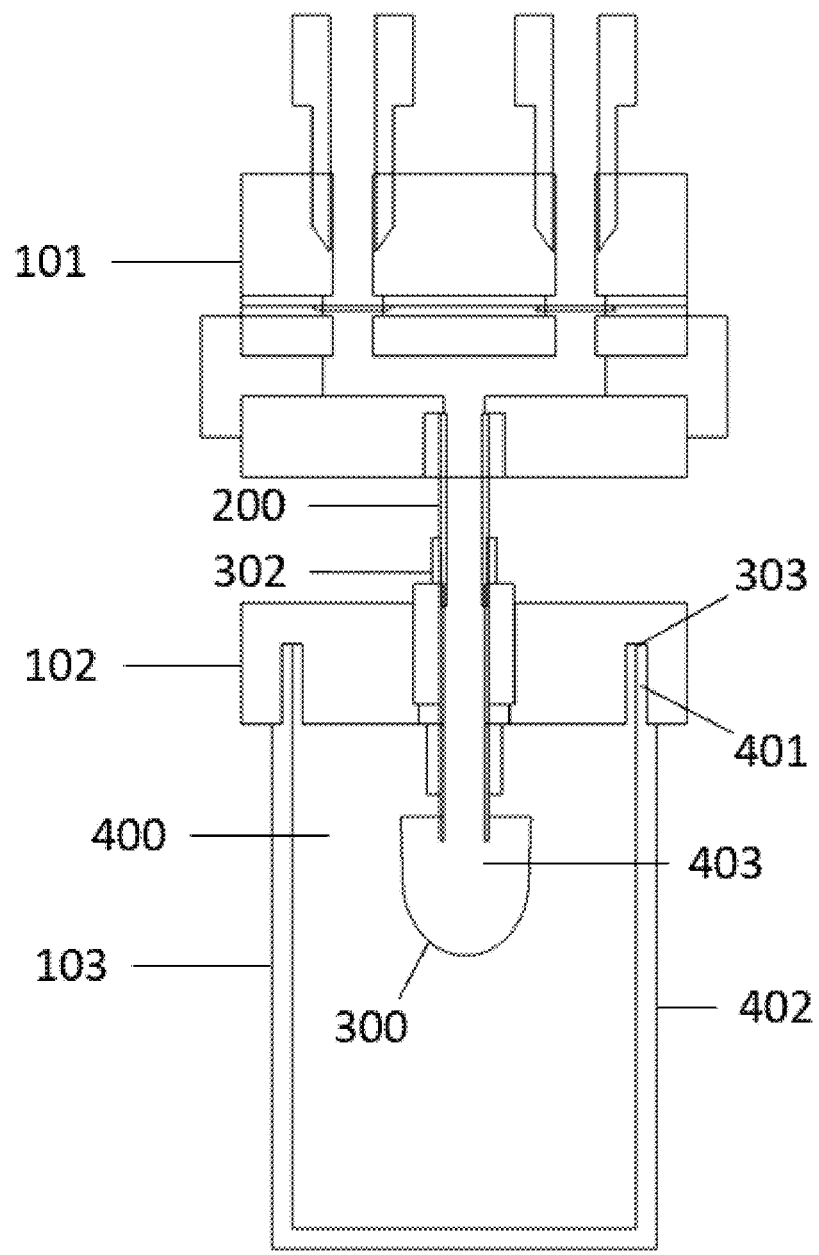
FIG. 4 illustrates the cross-sectional view of the OC bioreactor in its assembled form.

In reference to FIG. 4, bottom layer 103 of OC bioreactor 100 is used to hold the volume of fluid 400 surrounding the external surface of OC 300. Bottom layer 103 can be made of polystyrene, glass, polycarbonate, or any material that is biocompatible and optically transparent. In some embodiments, the top surface of bottom layer 103 has an extension 401 that press-fits into groove 303 on the bottom surface of middle layer 102. In some embodiments, bottom layer 103 has at least one flat window 402 for viewing OC 300 from its side (i.e., an elevation view). The volume of fluid 400 within bottom layer 103 can be reduced by decreasing the height of bottom layer 103. Alternatively, an insert can be placed inside bottom layer 103 to displace fluid volume. Bottom layer 103 may have its own system of ports or valves for exchanging fluids or adding compounds of interest. Bottom layer 103 may have a system for electrically stimulating the organoid or tissue(s) using electrodes. In typical embodiments, these electrodes substitute for electrodes 306. The bottom layer may have a system for sensing changes in the electrophysiology of the organoid or tissue(s) by positioning sensing electrodes in close proximity to the OC 300.

In various embodiments, any leak-free connection known in the art is made between fluid channels in the various layers of bioreactor 100. Preferably, these connections are reversible. In exemplary embodiments, a Luer fitting, e.g., a male Luer-slip end 200, of top layer 101 and a Luer fitting, e.g., a female Luer-lock end 302, of middle layer 102 are used as secure but easily reversible fluidic connectors between the two layers. More generally, the disclosure comprehends any set of mating fittings to establish leak-free fluid channels, including placing male Luer-slip end 200 on the top surface of middle layer 102 to fit with female Luer-slip end 302 on the bottom surface of top layer 101. Other methods of attachment may be used, such as a threaded screw, magnetic connectors, or using a geometric design that allows the layers to snap together. The connected fluidic system creates an internal volume 403 within OC 300 that is separated from external volume 400 by OC 300 itself, which may comprise any internal or external non-biological lining material that, in combination with the organoid or tissues, comprise the wall of OC 300. In some embodiments, the lining material is a support material for the organoid or tissue(s). An exemplary lining material is an elastic balloon, which can also function as a support material for the organoid or tissue(s). The lining material (e.g., support material) is present during fabrication or formation of the organoid or tissue(s), and may be retained during use of OC 300, such as in modeling a disease for observation of disease progress, for testing compounds for efficacy, and/or for testing compounds for toxicity. In some embodiments, the non-biological lining material (e.g., support material) is removed once fabrication of the organoid or tissue is accomplished, and monitoring or testing of the organoid or tissue(s) is performed without the lining material.

Figure 5:
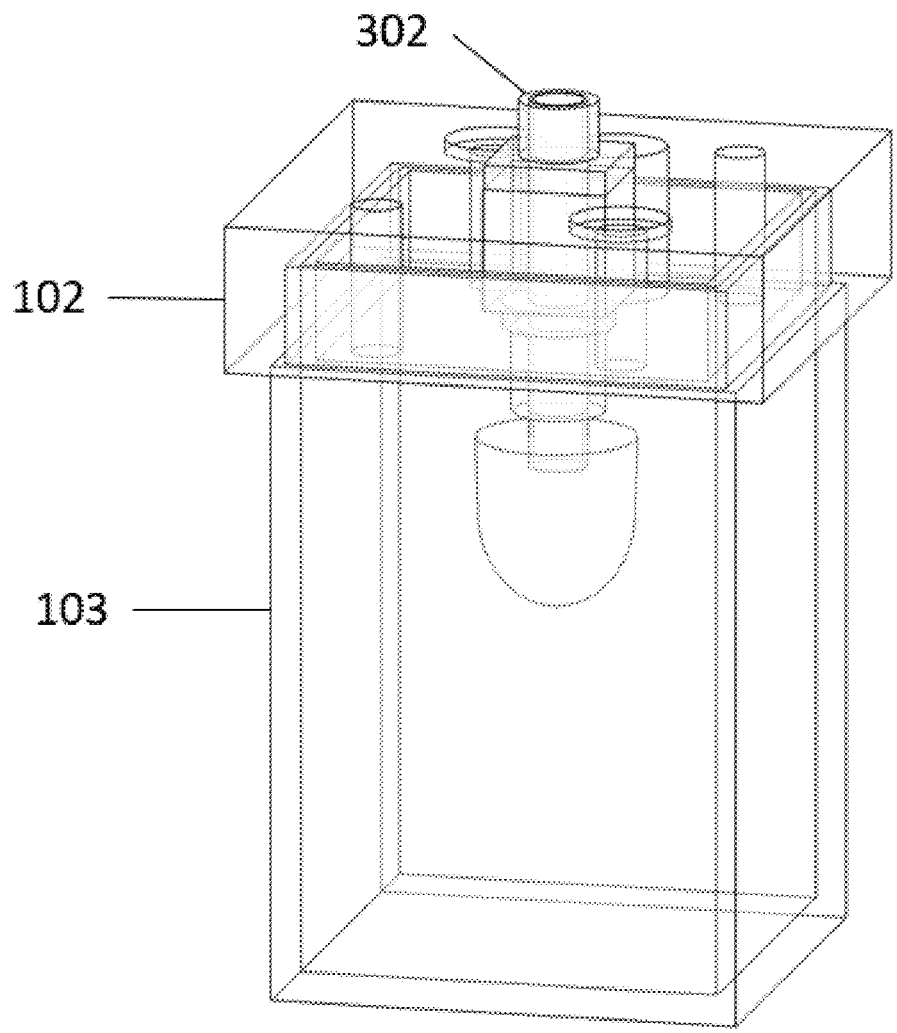
FIG. 5 illustrates the OC bioreactor with the minimal parts required for OC culture.

In reference to FIG. 5, OC bioreactor 100 can be adapted for culturing the organoid or tissue(s) within OC 300 in a standard incubator using only middle layer 102 and bottom layer 103. Hydrostatic pressure can be applied to OC 300 in this configuration by adding fluid, in an exemplary preferred embodiment, from female Luer-lock end 302 of middle layer 102. Alternatively, internal pressure can be applied by inflating and sealing (e.g., with a valve) OC 300, for example in embodiments wherein OC 300 comprises an organoid and/or tissue(s) and an elastomeric material such as a balloon. A custom rack may be used to transport and culture an array of OC bioreactor 100s for high-throughput fabrication and maintenance of multiple OC 300s.

A system for measuring the electrophysiology of the organoid or tissue(s) within OC 300 may be integrated into OC bioreactor 100. Such a system would use sensing electrodes to measure the extracellular potential of the organoid or tissue(s) in OC 300. In one embodiment, the sensing electrodes would be in direct contact with OC 300, either by contacting or embedding the electrodes on the balloon on the internal surface of OC 300 or by positioning the electrodes on the external surface of OC 300. In another embodiment, the sensing electrodes are positioned in OC bioreactor 100 without direct contact with OC 300 and the electrodes sense the aggregate electrical signal from OC 300 in a manner similar to an electrocardiogram.

A system compatible with OC bioreactor 100 is used to measure the volume of OC 300. In one embodiment, a camera is used to image OC 300 from the side (i.e., elevation view) to determine the cross-sectional projected area. Based on the geometry of OC 300, its volume is calculated by incorporating consideration of its cross-sectional area. In another embodiment, a pressure-volume catheter transducer is placed within internal volume 403 of OC 300 to measure the volume of OC 300. In another embodiment, the flow of the internal fluid is measured using an in-line flow meter to calculate changes in OC 300 volume. In another embodiment, fiducial markers are embedded or attached to the surface of OC 300 (either directly on the tissue or on the balloon surface) and tracked optically, magnetically, or by any method known in the art to determine OC 300 volume. In another embodiment, an ultrasonic transducer is used to image OC 300. In another embodiment, a laser-based detection system is used to monitor changes in OC 300 size and shape. More generally, any method or technique known in the art is used to detect or measure changes in OC 300 shape and/or volume.

A system for controlling the pressure within OC 300 may be integrated into OC bioreactor 100. Due to the design of top layer 101 providing for inlet 201 and outlet 202 that is separated by one or more valves, the fluidic preload and afterload can be independently controlled and applied to OC bioreactor 100. In one embodiment, a commercial pressure controller is used to control the applied pressure. Such a system can automate the control of applied pressure and apply dynamic pressures that mimic cardiac physiology. In another embodiment, the applied pressure is controlled using hydrostatic pressure. In another embodiment, the applied pressure is controlled using a variety of pump systems.

REFERENCES

Shah, R. R., Can pharmacogenetics help rescue drugs withdrawn from the market?, Pharmacogenomics. 7 (2006) 889-908. doi:10.2217/14622416.7.6.889

DiMasi, J. A., Grabowski, H. G. & Hansen, R. W. Innovation in the pharmaceutical industry: New estimates of R&D costs. J. Health Econ. 47, 20-33 (2016).

Mercola, M., Colas, A., Willems, E., Induced pluripotent stem cells in cardiovascular drug discovery, Circ. Res. 112 (2013) 534-548. doi:10.1161/CIRCRESAHA.111.250266

Passier, R., Orlova, V., Mummery, C., Complex Tissue and Disease Modeling using hiPSCs. Cell Stem Cell 18, (2016) 309-321. doi:10.1016/j.stem.2016.02.011

Li, R. A., Keung, W., Cashman, T. J., Backeris, P. C., Johnson, B. V., Bardot, E. S., Wong, A. O. T., Chan, P. K. W., Chan, C. W. Y., Costa, K. D., Bioengineering an electromechanically functional miniature ventricular heart chamber from human pluripotent stem cells. Biomaterials 163, (2018) 116-127. doi:10.1016/j.biomaterials.2018.02.024

Embodiments

Embodiment 1. A bioreactor for an organoid or tissue derived from a hollow organ comprising:
(a) a top layer for directing fluid flow into and/or out of an organoid chamber comprising an organoid or tissue;
(b) a middle layer, wherein the middle layer comprises the point of attachment for the organoid chamber; and
(c) a bottom layer comprising a reservoir for culture fluid;
wherein the top layer and middle layer are in fluid communication capable of exchanging an internal fluid,
wherein the top layer, middle layer and bottom layer are in fluid communication capable of exchanging an external fluid; and
wherein the organoid or tissue comprises a barrier between the internal fluid and the external fluid.

Embodiment 2. The bioreactor of Embodiment 1 wherein the organoid chamber further comprises an elastomeric lining material providing an impermeable barrier between the internal fluid and the external fluid.

Embodiment 3. The bioreactor of Embodiment 2 wherein the elastomeric material is a balloon.

Embodiment 4. The bioreactor of Embodiment 1 wherein the organoid or tissue is derived from cells of a heart, a lung, a gall bladder, a urinary bladder, a blood vessel, a lymph vessel, a ureter, a urethra, a small intestine, or a colon.

Embodiment 5. The bioreactor of Embodiment 4 wherein the cells are derived from pluripotent stem cells.

Embodiment 6. The bioreactor of Embodiment 1 wherein the top layer comprises a bottom surface comprising a Luer fitting terminating a fluid channel in the top layer, wherein the Luer fitting connects to the top surface of the middle layer, thereby providing a channel for fluid communication between the top layer and the middle layer.

Embodiment 7. The bioreactor of Embodiment 6 wherein the fluid channel in the top layer terminates in an inlet port and in an outlet port in the top surface of the top layer.

Embodiment 8. The bioreactor of Embodiment 7 further comprising a first flangeless fitting for connecting the inlet port to an external fluidic line and a second flangeless fitting for connecting the outlet port to a second external fluidic line.

Embodiment 9. The bioreactor of Embodiment 7 further comprising at least one valve to control the flow of fluid in the channel of the top layer.

Embodiment 10. The bioreactor of Embodiment 9 wherein the at least one valve allows one-way fluid flow from the inlet port to the outlet port.

Embodiment 11. The bioreactor of Embodiment 9 further comprising two layers of a plastic or metal sheet containing a valve layer therebetween, wherein the valve layer comprises the at least one valve to control the flow of fluid.

Embodiment 12. The bioreactor of Embodiment 11 wherein the plastic sheet is a polycarbonate sheet.

Embodiment 13. The bioreactor of Embodiment 11 wherein a gasket is interposed between the valve layer and each layer of plastic or metal sheet.

Embodiment 14. The bioreactor of Embodiment 11 wherein the two layers of plastic or metal sheet and the valve layer are attached using fasteners, a solvent, a sealant, or glue.

Embodiment 15. The bioreactor of Embodiment 14 wherein the fasteners are screws, threaded inserts, nut traps, clamps, latches, snap fittings, or press fittings.

Embodiment 16. The bioreactor of Embodiment 1 wherein the top layer further comprises a measurement channel for a measurement device, wherein the measurement channel is in fluid communication with the internal fluid channel of the top layer, and wherein the measurement channel terminates at a side surface of the top layer in a measurement port.

Embodiment 17. The bioreactor of Embodiment 16 wherein the measurement channel comprises a measurement device.

Embodiment 18. The bioreactor of Embodiment 17 wherein the measurement device is a pressure transducer.

Embodiment 19. The bioreactor of Embodiment 1 wherein the living cells form the organoid or at least one tissue around the elastomeric material.

Embodiment 20. The bioreactor of Embodiment 1 further comprising a blunt needle that terminates in an internal volume of the organoid chamber and traverses the middle layer of the bioreactor.

Embodiment 21. The bioreactor of Embodiment 1 wherein the bottom surface of the middle layer and the top surface of the bottom layer provide mating surfaces that register the surfaces relative to each other.

Embodiment 22. The bioreactor of Embodiment 21 wherein the bottom surface of the middle layer comprises a groove and the top surface of the bottom layer comprises a complementary mating surface to the bottom surface of the middle layer comprising the groove, or wherein the top surface of the bottom layer comprises a groove and the bottom surface of the middle layer comprises a complementary mating surface to the top surface of the bottom layer comprising the groove.

Embodiment 23. The bioreactor of Embodiment 1 wherein the middle layer is fabricated from a single sheet of plastic or metal.

Embodiment 24. The bioreactor of Embodiment 23 wherein the plastic is polycarbonate.

Embodiment 25. The bioreactor of Embodiment 1 wherein the middle layer further comprises a perfusion inlet port and a perfusion outlet port.

Embodiment 26. The bioreactor of Embodiment 1 wherein the middle layer further comprises an electrical system comprising at least one electrode, wherein each electrode is positioned to provide an electrical stimulation to the organoid chamber, to electrically record a signal from the organoid chamber, or both.

Embodiment 27. The bioreactor of Embodiment 26 wherein at least one electrode is in contact with the organoid chamber.

Embodiment 28. The bioreactor of Embodiment 26 wherein each electrode is made of carbon, platinum, or gold.

Embodiment 29. The bioreactor of Embodiment 26 wherein two electrodes are disposed 180 degrees from each other.

Embodiment 30. The bioreactor of Embodiment 26 wherein each electrode is positioned by at least one O-ring.

Embodiment 31. The bioreactor of Embodiment 26 wherein the at least one electrode is a bipolar electrode (a) in contact with the exterior surface of the organoid chamber comprising the organoid or at least one tissue, or (b) integrated into a point where the blunt needle is attached to the middle layer.

Embodiment 32. The bioreactor of Embodiment 1 wherein the middle layer further comprises a system for sensing electrophysiological changes in the organoid or tissue of the organoid chamber.

Embodiment 33. The bioreactor of Embodiment 1 wherein the bottom layer comprises culture fluid in contact with the exterior of the organoid chamber.

Embodiment 34. The bioreactor of Embodiment 1 wherein the bottom layer is composed of a material that is biocompatible and optically transparent.

Embodiment 35. The bioreactor of Embodiment 34 wherein the material is acrylic, polystyrene, glass or polycarbonate.

Embodiment 36. The bioreactor of Embodiment 1 wherein the bottom layer further comprises at least one flat window for observation of the organoid chamber.

Embodiment 37. The bioreactor of Embodiment 1 wherein the bottom layer comprises at least one port, at least one valve, or at least one port and at least one valve, wherein the at least one port and/or at least one valve provides for exchanging fluid or adding at least one compound.

Embodiment 38. The bioreactor of Embodiment 1 wherein the bottom layer comprises an electrode for stimulating the organoid or tissue.

Embodiment 39. The bioreactor of Embodiment 1 wherein fluid channels in different layers are connected using Luer fittings, threaded connectors, magnetic connectors or a snap-fit geometric design.

Embodiment 40. The bioreactor of Embodiment 39 wherein a male Luer-slip end at the bottom surface of the top layer is connected to a female Luer-lock end at the top surface of the middle layer.

Embodiment 41. The bioreactor of Embodiment 1 wherein the middle layer and the bottom layer are sufficient to culture the organoid or tissue in an incubator.

Embodiment 42. The bioreactor of Embodiment 1 further comprising a system for measuring an electrophysiological property of the organoid or tissue.

Embodiment 43. The bioreactor of Embodiment 42 wherein the system comprises at least one sensing electrode for measuring the extracellular potential of the organoid or tissue in the organoid chamber.

Embodiment 44. The bioreactor of Embodiment 43 wherein the sensing electrode is in direct contact with the interior or exterior of the organoid chamber.

Embodiment 45. The bioreactor of Embodiment 37 wherein there are a plurality of sensing electrodes that do not directly contact the organoid chamber, wherein the plurality of sensing electrodes detect the electrical signal from the organoid chamber.

Embodiment 46. The bioreactor of Embodiment 1 wherein the point of attachment for the organoid chamber comprises a blunt needle attached at one end to the middle layer and attached at the other end to the organoid chamber.

Embodiment 47. Use of the bioreactor of Embodiments 1-45 to culture, maintain, stimulate, monitor or assay the organoid or tissue in the organoid chamber.

Embodiment 48. The use of Embodiment 47 comprising addition of a compound to the culture medium and observation of the effect on the organoid or tissue, thereby assaying the compound for a biological effect.

Embodiment 49. The use of Embodiment 48 wherein the effect is an altered organoid or tissue stiffness, pressure, volume, or growth rate.

Embodiment 50. The use of Embodiment 48 wherein the effect is an alteration in electrophysiology.

Embodiment 51. The use of Embodiment 48 wherein the organoid or tissue is a cardiac organoid or tissue.

Embodiment 52. A system to measure the volume of or pressure experienced by an organoid chamber comprising the bioreactor of Embodiments 1-46 and a measurement device.

Embodiment 53. The system of Embodiment 52 wherein the device to measure volume is a camera, a pressure-volume catheter placed into the interior volume of the organoid chamber, a flow meter for measuring internal fluid flow, or an ultrasonic transducer to image the organoid chamber.

Embodiment 54. The system of Embodiment 53 wherein the device to measure volume is a camera, the system further comprising at least one fiducial marker attached to the surface of the organoid chamber.

Embodiment 55. The system of Embodiment 54 wherein the at least one fiducial marker is tracked optically or magnetically.

Embodiment 56. The system of Embodiment 52 wherein the pressure is measured by a pressure transducer.

Embodiment 57. A system for controlling pressure within an organoid chamber comprising the bioreactor of Embodiments 1-46 and a pressure controller attached to the inlet port of the top layer, to the outlet port of the top layer or to both the inlet and outlet ports of the top layer, to regulate the fluid pressure applied to the organoid chamber.

Embodiment 58. The system of Embodiment 57 wherein the organoid is a cardiac organoid and wherein the pressure applied to the organoid chamber is automatically controlled.

Embodiment 59. The system of Embodiment 58 wherein the pressure is dynamically controlled to mimic cardiac physiology.

Embodiment 60. The system of Embodiment 57 wherein the pressure is controlled using hydrostatic pressure or using at least one fluid pump.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A bioreactor for an organoid or tissue derived from a hollow organ comprising:
   an organoid chamber comprising an organoid or tissue including:
   (a) a top layer configured to direct fluid flow into and/or out of the organoid chamber;
   (b) a middle layer comprising a point of attachment for the organoid chamber; and
   (c) a bottom layer comprising a reservoir for culture fluid;
   wherein the top layer and middle layer are in fluid communication capable of exchanging an internal fluid,
   wherein the top layer, middle layer and bottom layer are in fluid communication capable of exchanging an external fluid;
   wherein the top layer, middle layer and bottom layer include fluid channels that are connected using at least one Luer connection; and
   wherein the organoid chamber comprises an elastomeric material providing a barrier between the internal fluid and the external fluid wherein the elastomeric material is a balloon.

2. The bioreactor of claim 1, wherein the barrier between the internal fluid and the external fluid is an impermeable barrier.

3. The bioreactor of claim 1, wherein the organoid or tissue is derived from cells of a heart, a lung, a gall bladder, a urinary bladder, a blood vessel, a lymph vessel, a ureter, a urethra, a small intestine, a colon, or comprises pluripotent stem cells or cell types derived from these.

4. The bioreactor of claim 1, wherein the top layer comprises a bottom surface comprising a Luer fitting terminating a fluid channel in the top layer, wherein the Luer fitting connects to the top surface of the middle layer, thereby providing a channel for fluid communication between the top layer and the middle layer.

5. The bioreactor of claim 4, wherein the fluid channel in the top layer terminates in an inlet port and in an outlet port in the top surface of the top layer.

6. The bioreactor of claim 5, further comprising at least one valve to control the flow of fluid in the channel of the top layer thereby allowing one-way fluid flow from the inlet port to the outlet port.

7. The bioreactor of claim 1, further comprising two layers of a plastic or metal sheet containing a valve layer therebetween, wherein the valve layer comprises at least one valve to control the flow of fluid.

8. The bioreactor of claim 7, wherein a gasket is interposed between the valve layer and each layer of plastic or metal sheet.

9. The bioreactor of claim 1, wherein the top layer further comprises a measurement channel for a measurement device, wherein the measurement channel is in fluid communication with an internal fluid channel of the top layer, and wherein the measurement channel terminates at a side surface of the top layer in a measurement port.

10. The bioreactor of claim 9, wherein the measurement device is a pressure transducer.

11. The bioreactor of claim 1, wherein living cells form the organoid or at least one tissue around the elastomeric material.

12. The bioreactor of claim 1, further comprising a blunt needle that terminates in an internal volume of the organoid chamber and traverses the middle layer of the bioreactor.

13. The bioreactor of claim 1, wherein the bottom surface of the middle layer comprises a groove and the top surface of the bottom layer comprises a complementary mating surface to the bottom surface of the middle layer comprising the groove, or wherein the top surface of the bottom layer comprises a groove and the bottom surface of the middle layer comprises a complementary mating surface to the top surface of the bottom layer comprising the groove.

14. The bioreactor of claim 1, wherein the middle layer further comprises a perfusion inlet port and a perfusion outlet port for adding at least one compound.

15. The bioreactor of claim 1, wherein the middle layer further comprises an electrical system comprising at least one electrode, wherein each electrode is positioned to provide an electrical stimulation to the organoid chamber, to electrically record a signal from the organoid chamber, or both.

16. The bioreactor of claim 1, wherein the bottom layer comprises culture fluid in contact with the exterior of the organoid chamber.

17. The bioreactor of claim 1, wherein the bottom layer further comprises at least one flat window that is optically transparent for observation of the organoid chamber.

18. The bioreactor of claim 1, wherein the bottom layer comprises at least one port, at least one valve, or at least one port and at least one valve, wherein the at least one port and/or at least one valve provides for exchanging fluid or adding at least one compound.

19. A system to measure the volume of or pressure experienced by an organoid chamber comprising the bioreactor of claim 1 and a measurement device.

20. The system of claim 19 wherein the measurement device is a camera, a pressure-volume catheter placed into the interior volume of the organoid chamber, a flow meter for measuring internal fluid flow, or an ultrasonic transducer to image the organoid chamber.

21. A system for controlling pressure within an organoid chamber comprising the bioreactor of claim 1 and a pressure controller attached to an inlet port of the top layer, to an outlet port of the top layer or to both the inlet and outlet ports of the top layer, to regulate the fluid pressure applied to the organoid chamber.

* * * * *